US012083284B2

(12) United States Patent
Lin et al.

(10) Patent No.: US 12,083,284 B2
(45) Date of Patent: Sep. 10, 2024

(54) RESPIRATORY SYSTEM

(71) Applicant: APEX MEDICAL CORP., New Taipei (TW)

(72) Inventors: Chun-Yen Lin, New Taipei (TW); Chung-Yi Lin, New Taipei (TW); Jhih-Teng Yao, New Taipei (TW); Chih-Tsan Chien, New Taipei (TW); Tsung-Chung Kan, New Taipei (TW); Hao-Yu Chan, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 814 days.

(21) Appl. No.: 17/032,976

(22) Filed: Sep. 25, 2020

(65) Prior Publication Data

US 2021/0093825 A1  Apr. 1, 2021

(30) Foreign Application Priority Data

Sep. 27, 2019  (TW) .................................. 108135108

(51) Int. Cl.
*A61M 16/10* (2006.01)
*A61M 16/00* (2006.01)
*A61M 16/08* (2006.01)
*A61M 16/16* (2006.01)

(52) U.S. Cl.
CPC ...... *A61M 16/1045* (2013.01); *A61M 16/021* (2017.08); *A61M 16/0816* (2013.01); *A61M 16/162* (2013.01)

(58) Field of Classification Search
CPC ............ A61M 16/1045; A61M 16/021; A61M 16/0816; A61M 16/16; A61M 16/109; A61M 16/1095; A61M 16/161; A61M 2205/3633
See application file for complete search history.

(56) References Cited

U.S. PATENT DOCUMENTS

| | | | | |
|---|---|---|---|---|
| 10,980,966 | B2* | 4/2021 | DiMatteo | ............... A61M 16/14 |
| 11,278,689 | B2* | 3/2022 | Hermez | ............... A61M 16/024 |
| 2007/0132117 | A1* | 6/2007 | Pujol | .................... A61M 16/208 |
| | | | | 261/119.1 |
| 2007/0169776 | A1* | 7/2007 | Kepler | ................ A61M 16/107 |
| | | | | 128/200.14 |
| 2007/0230927 | A1* | 10/2007 | Kramer | ............... A61M 16/109 |
| | | | | 392/403 |

(Continued)

*Primary Examiner* — Colin W Stuart
*Assistant Examiner* — Douglas Y Sul
(74) *Attorney, Agent, or Firm* — Muncy, Geissler, Olds & Lowe, P.C.

(57) ABSTRACT

A respiratory system includes a gas supply unit and a heating and humidifying unit. The gas supply unit includes a gas supply port; the heating and humidifying unit is detachably combined with the gas supply unit. The heating and humidifying unit includes a base, an adapter and a water tank. The base includes a control element, and the adapter is combined with the base and can rotate at least 90 degrees relative to the base. The water tank is detachably combined with the base, and the water tank includes a gas inlet and a gas outlet, wherein when the water tank is combined with the base, the gas inlet penetrates through an aperture of the base to be fluidly connected to the gas supply port, and the gas outlet is fluidly connected to the adapter.

20 Claims, 11 Drawing Sheets

(56) References Cited

U.S. PATENT DOCUMENTS

| | | | | |
|---|---|---|---|---|
| 2011/0155132 A1* | 6/2011 | Virr | ............ | A61M 16/16 |
| | | | | 128/203.26 |
| 2014/0332003 A1* | 11/2014 | Crumblin | ......... | A61M 16/0875 |
| | | | | 128/207.14 |
| 2015/0273167 A1* | 10/2015 | Feldhahn | ............ | A61M 16/021 |
| | | | | 128/204.21 |
| 2016/0199612 A1* | 7/2016 | Foote | ................ | A61M 16/0875 |
| | | | | 128/202.27 |
| 2016/0310691 A1* | 10/2016 | Bath | ...................... | G16H 20/40 |
| 2018/0169322 A1* | 6/2018 | Chiu | .................... | A61M 5/1413 |
| 2020/0330720 A1* | 10/2020 | Formica | .............. | A61M 16/109 |
| 2021/0008325 A1* | 1/2021 | Spence | ................. | A61M 16/16 |
| 2021/0228833 A1* | 7/2021 | Alshut | ................ | A61M 16/162 |

\* cited by examiner

RESPIRATORY SYSTEM

This application claims the priority benefits of Taiwan Patent Application No. 108135108, filed on Sep. 27, 2019. The entirety the above-mentioned patent application is hereby incorporated by reference herein and made a part of this specification.

BACKGROUND

1. Field of the Disclosure

The present disclosure relates to a respiratory system and more particularly to a respiratory system with separable different functional units.

2. Description of Related Art

A traditional respiratory system only inhales outside air and produces breathing gas that can be supplied to the user. However, when the outside air is too dry or the temperature of the user's environment is low, the produced breathing gas will lack moisture or have a low temperature. Therefore, how to provide stable humidity and temperature for the breathing gas produced by the respiratory system is particularly important.

In addition, many respiratory systems adopt a separable design for only the water tank in the overall structure. Once the primary component of the respiratory system fails, the user must replace it with a new component, which lacks flexibility in use and increases the cost. It is also inconvenient for the user.

SUMMARY

The purpose of the present disclosure is to provide a respiratory system with separable different functional units such that users can replace corresponding functional units according to different needs or conditions and thereby to increase the flexibility and convenience of such a system.

To achieve the aforesaid and other objects, the respiratory system of the present disclosure includes a gas supply unit and a heating and humidifying unit. The gas supply unit includes a gas supply port. The heating and humidifying unit is detachably combined with the gas supply unit, and the heating and humidifying unit is electrically connected to the gas supply unit when combined with the gas supply unit. The heating and humidifying unit includes a base, an adapter and a water tank. The base includes a control element, and the adapter is combined with the base and can rotate at least 90 degrees relative to the base. The adapter is electrically connected to the control element. The water tank is detachably combined with the base, and the water tank includes a gas inlet and a gas outlet. When the water tank is combined with the base, the gas inlet penetrates through an aperture of the base to be fluidly connected to the gas supply port, and the gas outlet is fluidly connected to the adapter.

In one embodiment of the present disclosure, the respiratory system further includes a heated circuit, the heated circuit is detachably combined with the adapter, and an electrical connection and a fluid connection are formed between the heated circuit and the adapter when the heated circuit is combined with the adapter.

In one embodiment of the present disclosure, the adapter is electrically connected to the control element through an electrical connection wire, the adapter includes at least one wire restraint portion, and the electrical connection wire can be accommodated and wound around the at least one wire restraint portion to prevent the electrical connection wire from contacting and rubbing the base when the adapter rotates.

In one embodiment of the present disclosure, the base further includes a fixing portion for combining with the adapter, the fixing portion includes a through hole and an inner wall, and the inner wall protrudes from a surface of the base and surrounds the through hole.

In one embodiment of the present disclosure, the fixing portion further includes a groove and at least one drain hole, the groove surrounds the through hole and the inner wall is located between the groove and the through hole, and the at least one drain hole is located at a bottom of the groove.

In one embodiment of the present disclosure, the base further includes a pipe connector, the pipe connector is disposed under the fixing portion and forms a fluid connection between the water tank and the adapter, the pipe connector includes a water guiding portion, and a position of the water guiding portion is corresponded to a position of the at least one drain hole to receive the water flowing in from the at least one drain hole.

In one embodiment of the present disclosure, the base further includes a heating element, the water tank includes a reservoir and a heat conducting member corresponding to the heating element, and the heat conducting member is adjacent to the reservoir.

In one embodiment of the present disclosure, the water tank further includes a sleeve member, the sleeve member extends from the gas inlet portion toward the water tank to form a gas outlet end, and the sleeve member includes a buffer end sleeved on of the gas inlet portion such that the buffer end is directly connected to the gas supply port when the water tank is combined with the base to provide flow channel sealing and combination buffering effects.

In one embodiment of the present disclosure, the gas outlet end of the sleeve member is higher than the reservoir, and the gas outlet end forms a chamfered surface facing the reservoir.

In one embodiment of the present disclosure, a cross-sectional area of the sleeve member gradually increases from the buffer end to the gas outlet end.

In one embodiment of the present disclosure, the gas outlet end of the sleeve member is higher than the buffer end to prevent the water stored in the reservoir from flowing back to the gas outlet end.

In one embodiment of the present disclosure, the water tank includes at least one baffle for guiding the gas output from the gas outlet end to flow toward the reservoir.

In one embodiment of the present disclosure, the heating and humidifying unit further includes a shield member, and the shield member is pivotally and rotatably connected to the base and provides a protective effect for the base when the gas supply unit is separated from the heating and humidifying unit.

BRIEF DESCRIPTION OF THE DRAWINGS

The accompanying drawings are included to provide further understanding of the invention and are incorporated in and constitute a part of this specification. The drawings illustrate embodiments of the invention and, together with the descriptions, serve to explain the principles of the invention.

DESCRIPTION OF THE EMBODIMENTS

Since various aspects and embodiments are merely exemplary and not limiting, after reading this specification, skilled artisans should appreciate that other aspects and embodiments are possible without departing from the scope of the disclosure. Other features and benefits of any one or more of the embodiments will be apparent from the following detailed description and the claims.

As used herein, "a," "an" or similar expressions are employed to describe elements and components of the present disclosure. This is done merely for convenience and to give a general sense of the scope of the present disclosure. Accordingly, this description should be understood to include one or at least one, and the singular also includes the plural unless it is obvious that it means otherwise.

As used herein, ordinal numbers "first," "second," and the like are used for distinguishing between or referring to identical or similar components or structures and not necessarily for describing a sequential or chronological order thereof. It should be understood that ordinal numbers are interchangeable in some situations or configurations without affecting the implementation of the present disclosure.

As used herein, the terms "includes," "including," "has," "having" and any other variations thereof are intended to cover a non-exclusive inclusion. For example, a component or structure that includes a list of elements is not necessarily limited to only those elements but may include other elements not explicitly listed or inherent to such component or structure.

Figure 1:
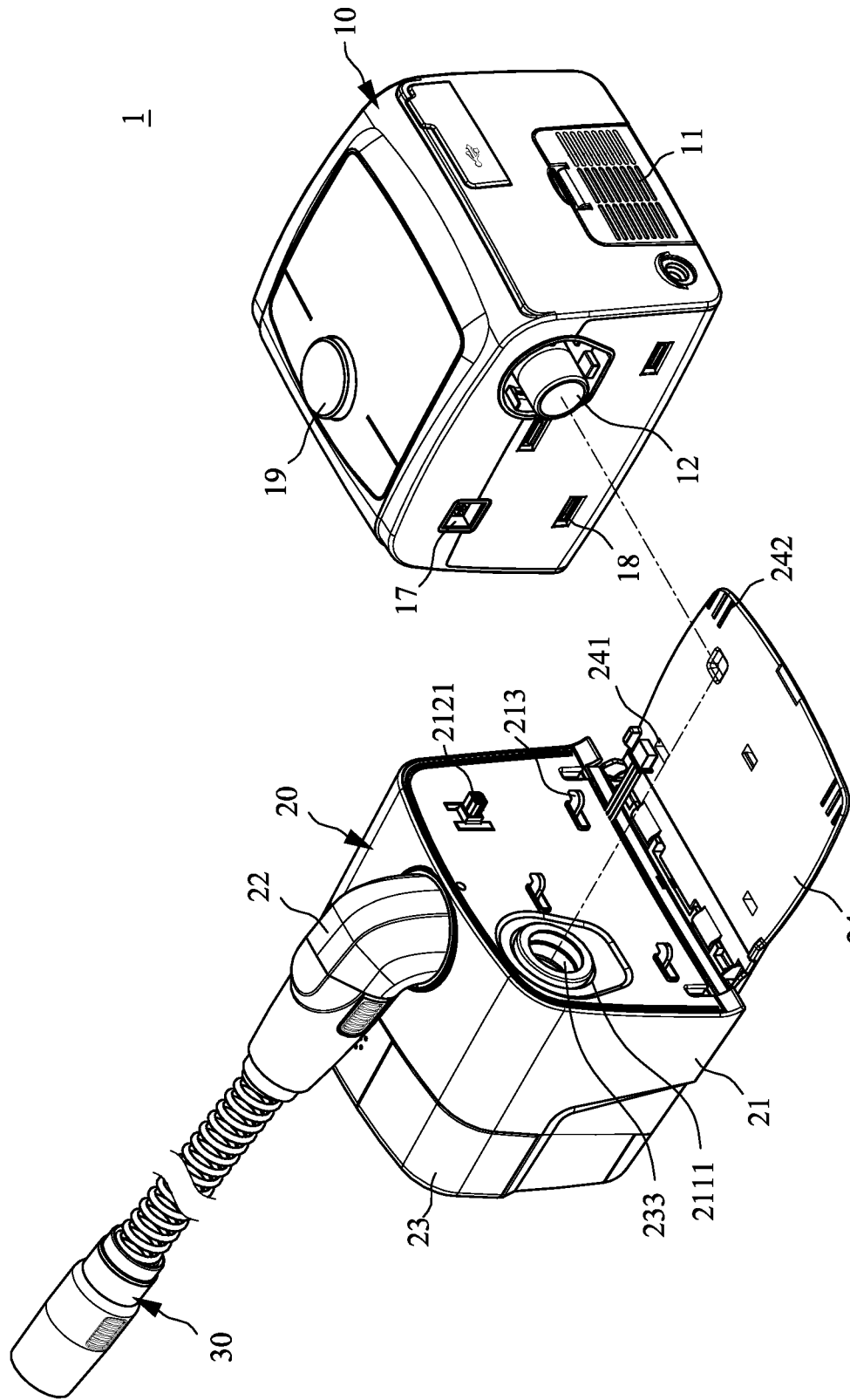
FIG. 1 illustrates a perspective view of the respiratory system of the present disclosure.
Figure 2:
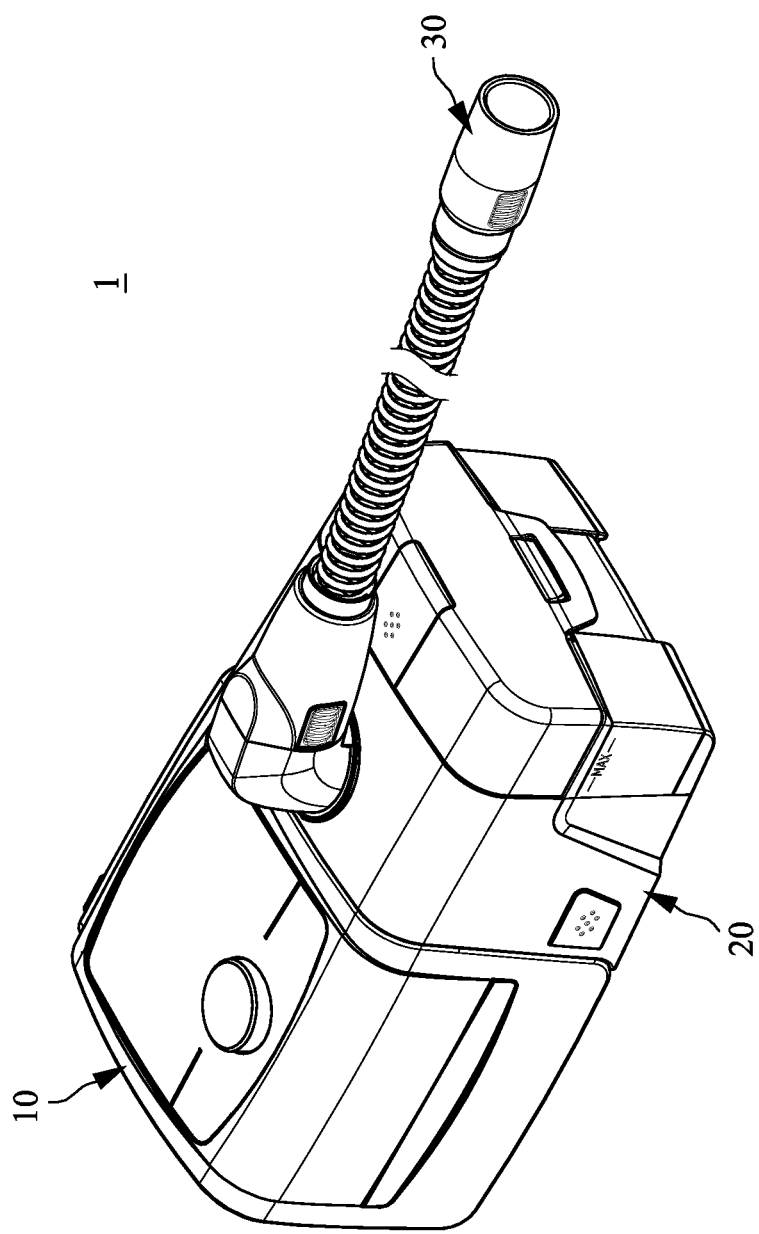
FIG. 2 illustrates a perspective view of the respiratory system of the present disclosure showing the gas supply unit and the heating and humidifying unit combined.
Figure 3:
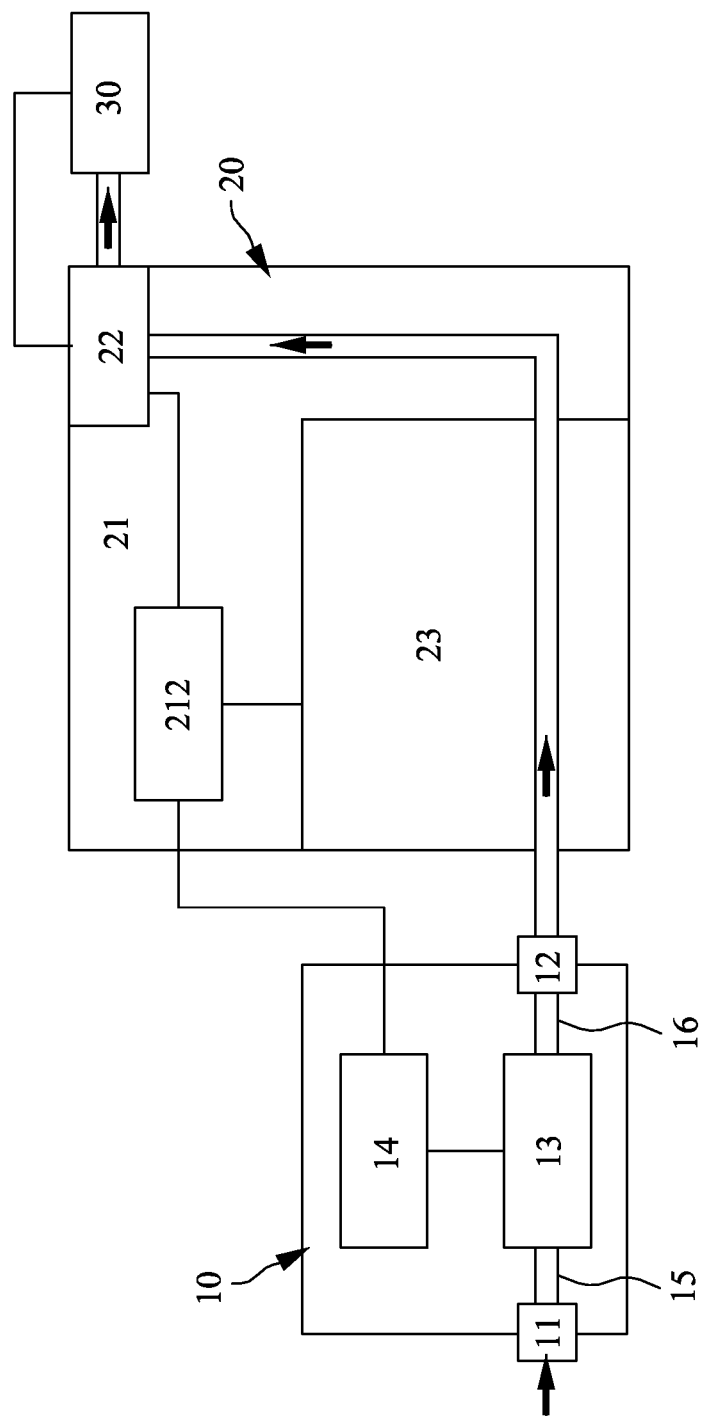
FIG. 3 illustrates a schematic diagram of the inside of the respiratory system of the present disclosure showing the gas supply unit and the heating and humidifying unit combined.

Please refer to FIG. 1 to FIG. 3 together. FIG. 1 illustrates a perspective view of the respiratory system 1 of the present disclosure, FIG. 2 illustrates a perspective view of the respiratory system 1 of the present disclosure showing the gas supply unit 10 and the heating and humidifying unit 20 combined, and FIG. 3 illustrates a schematic diagram of the inside of the respiratory system 1 of the present disclosure showing the gas supply unit 10 and the heating and humidifying unit 20 combined. As shown in FIG. 1 to FIG. 3, the respiratory system 1 of the present disclosure mainly includes a gas supply unit 10 and a heating and humidifying unit 20, and the heating and humidifying unit 20 can be detachably combined with the gas supply unit 10. When the gas supply unit 10 and the heating and humidifying unit 20 are separated, the gas supply unit 10 and the heating and humidifying unit 20 are independent structures respectively, as shown in FIG. 1. When the heating and humidifying unit 20 is combined with the gas supply unit 10, the heating and humidifying unit 20 and the gas supply unit 10 are electrically and fluidly connected to each other, as shown in FIG. 2 and FIG. 3. A fluid transmission path of the respiratory system 1 of the present disclosure is indicated by the direction of the thick arrow in FIG. 3. The gas supply unit 10 mainly supplies breathing gas, and the heating and humidifying unit 20 mainly heats and humidifies the breathing gas supplied by the gas supply unit 10.

In one embodiment of the present disclosure, the respiratory system 1 of the present disclosure further includes a heated circuit 30. The heated circuit 30 is detachably combined with the heating and humidifying unit 20. When the heated circuit 30 is combined with the heating and humidifying unit 20, an electrical connection and a fluid connection are formed between the heated circuit 30 and the heating and humidifying unit 20. Accordingly, the heated circuit 30 can output the breathing gas processed by the heating and humidifying unit 20, and the heated circuit 30 can heat the inside of the heated circuit 30 after power is supplied to maintain the temperature of the breathing gas flowing through the heated circuit 30 and accelerate the removal of the possible residual moisture inside the heated circuit 30.

As shown in FIG. 1 and FIG. 3, the gas supply unit 10 includes a gas suction port 11, a gas supply port 12, an airflow generator 13 and a controller 14. The gas suction port 11 and the gas supply port 12 are arranged on an outer casing of the gas supply unit 10, and the airflow generator 13 is fluidly connected to the gas suction port 11 and the gas supply port 12 through different gas channels 15 and 16 respectively. The gas supply port 12 is disposed on the side of the gas supply unit 10 engaging the heating and humidifying unit 20 such that the gas supply port 12 can be directly connected to a corresponding inlet structure of the heating and humidifying unit 20 to form a tight fluid connection when the gas supply unit 10 is combined with the heating and humidifying unit 20. The airflow generator 13 and the controller 14 are disposed inside the gas supply unit 10, and the airflow generator 13 and the controller 14 are electrically connected to each other. The controller 14 can receive operation signals to activate or deactivate the airflow generator 13. When the airflow generator 13 is activated, the airflow generator 13 draws in the air outside the gas supply unit 10 into the gas supply unit 10 through the gas suction port 11 and then outputs the air through the gas supply port 12.

In one embodiment of the present disclosure, the airflow generator 13 may be a motor, a pump or other components that can generate airflow, and the controller 14 may be a processor or the like, but the present disclosure is not limited thereto. At least one filter element can be disposed at the gas suction port 11 to filter the external air. In this embodiment, the gas supply unit 10 further includes at least one electrical connection port 17 and at least one engaging structure 18. The at least one electrical connection port 17 and the at least one engaging structure 18 are both disposed at the side of the heating and humidifying unit 20 engaging the gas supply unit 10. The at least one electrical connection port 17 is electrically connected to the controller 14, and the at least one electrical connection port 17 is electrically connected to the heating and humidifying unit 20 when the gas supply unit 10 is combined with the heating and humidifying unit 20. The at least one engaging structure 18 is configured to help combine the gas supply unit 10 with the heating and humidifying unit 20.

The gas supply unit 10 may further include an operating part 19. The operating part 19 can be disposed with a power switch or/and at least one functional button or an operating panel for the user to perform corresponding operations according to requirements. In addition, the gas supply unit 10 can be equipped with different types of electrical connection ports, such as a memory slot, a USB slot, an external power port, etc., to meet different usage requirements.

The heating and humidifying unit 20 includes a base 21, an adapter 22, and a water tank 23. The heating and humidifying unit 20 is mainly combined with the gas supply unit 10 through the base 21 and is directly fluidly connected to the gas supply unit 10 through the water tank 23. The base 21 is mainly configured as a signal transmission interface and a structural combination with the gas supply unit 10. The water tank 23 is mainly configured as a water storage space and forms a fluid transmission path that can provide heating and humidification functions. The adapter 22 is configured as a fluid and electrical signal transmission interface for connecting the heating and humidifying unit 20 to the heated circuit 30.

Figure 4:
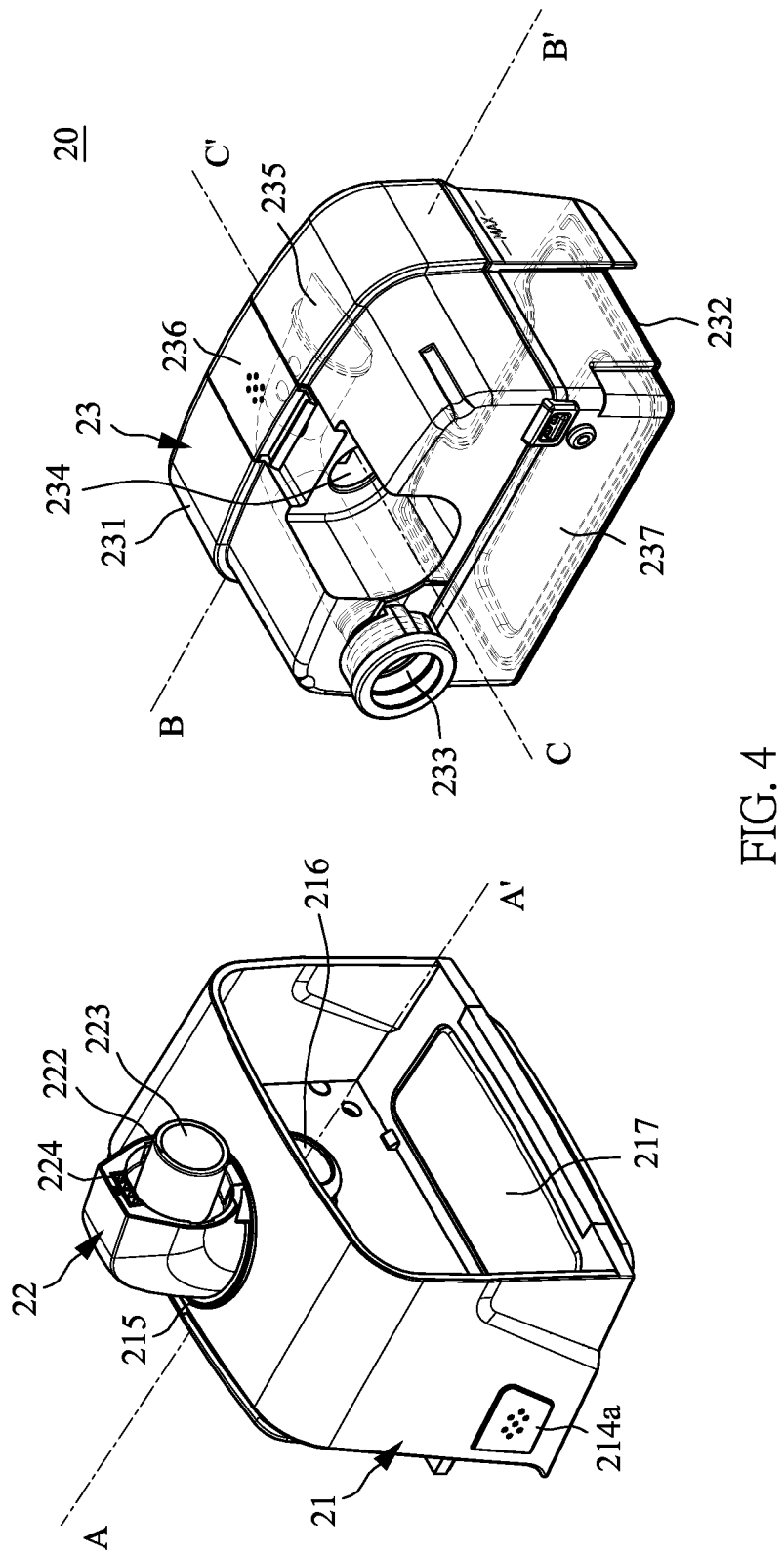
FIG. 4 illustrates a perspective view of the heating and humidifying unit of the respiratory system of the present disclosure showing the base and the water tank separated.
Figure 5:
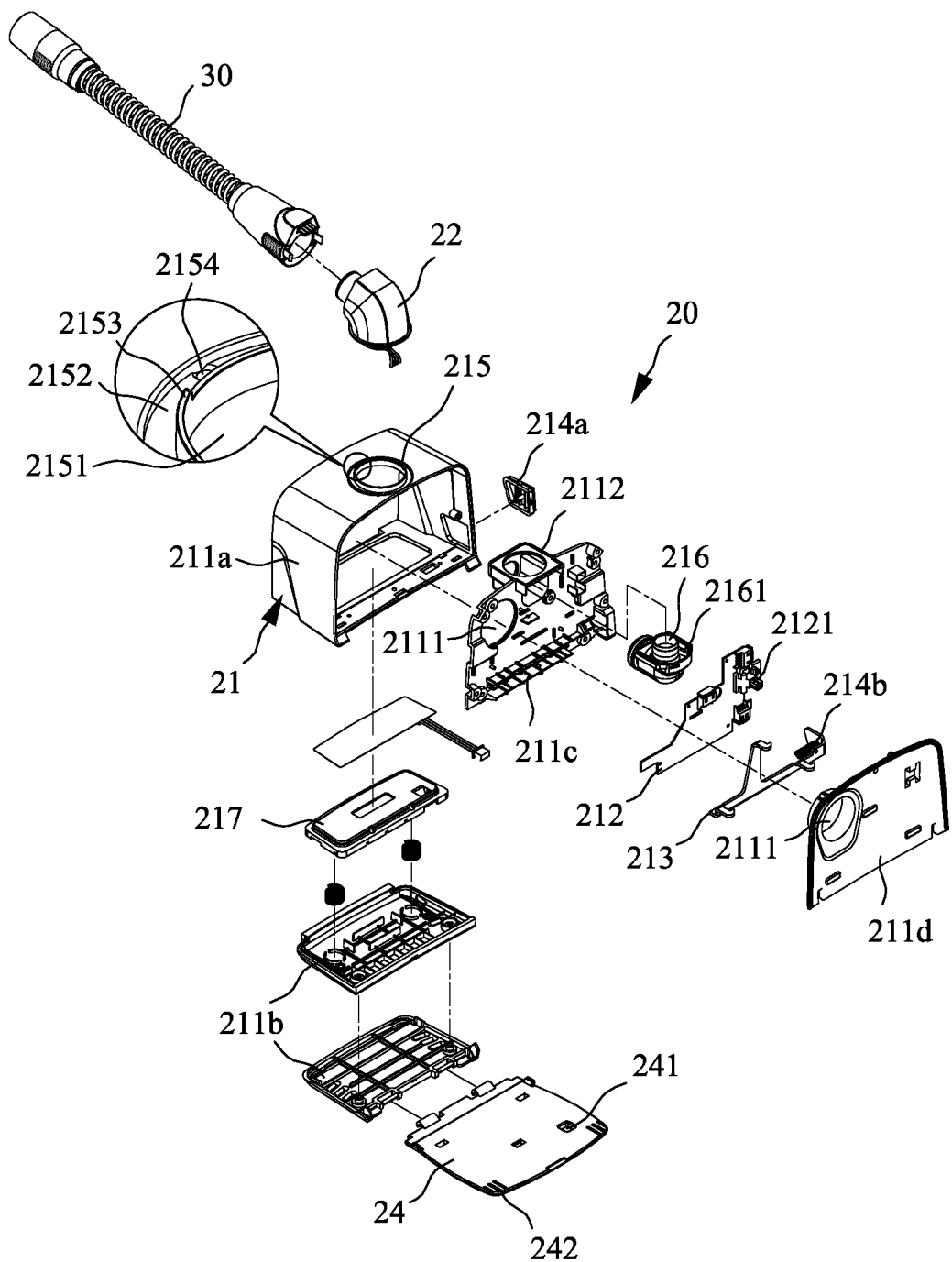
FIG. 5 illustrates an exploded view of the base of the heating and humidifying unit of the respiratory system of the present disclosure.
Figure 6:
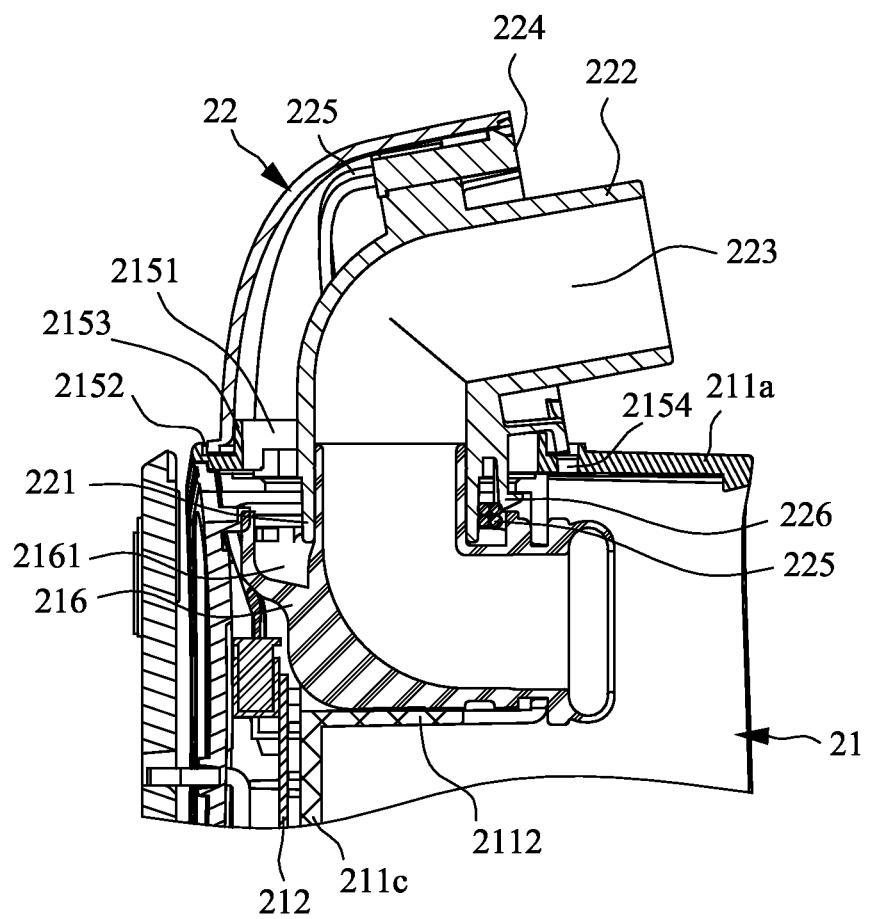
FIG. 6 illustrates a partial cross-sectional view of the base and the adapter of the respiratory system of the present disclosure along the line A-A' in FIG. 4.

The heating and humidifying unit 20 of the respiratory system 1 of the present disclosure will be described in detail below. Please refer to FIG. 4 to FIG. 6 together, where FIG. 4 illustrates a perspective view of the heating and humidifying unit 20 of the respiratory system 1 of the present disclosure showing the base 21 and the water tank 23 separated, FIG. 5 illustrates an exploded view of the base 21 of the heating and humidifying unit 20 of the respiratory system 1 of the present disclosure, and FIG. 6 illustrates a partial cross-sectional view of the base 21 and the adapter 22 of the respiratory system 1 of the present disclosure along the line A-A' in FIG. 4. As shown in FIG. 4, when the base 21 and the water tank 23 of the heating and humidifying unit 20 are separated, the base 21 and the water tank 23 are independent structures respectively, and the adapter 22 is combined with the base 21. Furthermore, as shown in FIG. 4 to FIG. 6, the base 21 of the heating and humidifying unit 20 includes housings 211*a* to 211*d*, a control element 212 and at least one corresponding engaging structure 213. An accommodating space is formed inside the housings 211*a* to 211*d*, and the control element 212 and the at least one corresponding engaging structure 213 are both disposed in the accommodating space. The housings 211*c* and 211*d* are two opposite housing parts. The housing 211*c* is located at the side of the base 21 engaging the water tank 23, and the housing 211*d* is located at the side of the base 21 engaging the gas supply unit 10.

In one embodiment of the present disclosure, the control element 212 may be a control circuit board for receiving or transmitting control commands or signals. The control element 212 includes at least one corresponding electrical connection port 2121. The at least one corresponding electrical connection port 2121 penetrates through the housing 211*d* and protrudes from the outer surface of the housing 211*d* to form an electrical connection with the at least one electrical connection port 17 of the gas supply unit 10. Disposing the control element 212 in the heating and humidifying unit 20 can reduce the cost of the gas supply unit 10 and reduce the number of pins of the corresponding electrical connection port 2121.

The at least one corresponding engaging structure 213 also penetrates the housing 211*d* and protrudes from the outer surface of the housing 211*d* so as to engage with the at least one engaging structure 18 of the gas supply unit 10. In this embodiment, the at least one corresponding engaging structure 213 can be driven to cause displacement by cooperating with the arrangement of a button 214*a* and an elastic member 214*b* such that the engagement state between the at least one corresponding engaging structure 213 of the base 21 and the at least one engagement structure 18 of the gas supply unit 10 is changed.

In one embodiment of the present disclosure, the housings 211*c* and 211*d* of the base 21 are provided with opposite apertures 2111. When the water tank 23 is combined with the base 21, the gas inlet 233 of the water tank 23 can penetrate through the apertures 2111 to form a fluid connection with the gas supply port 12 of the gas supply unit 10.

In one embodiment of the present disclosure, the base 21 further includes a fixing portion 215 for the combination of the adapter 22. The fixing portion 215 is disposed on the housing 211*a*, and the fixing portion 215 includes a through hole 2151, a groove 2152, an inner wall 2153 and at least one drain hole 2154. The groove 2152 is an annular groove surrounding the through hole 2151 and is configured to combine with the adapter 22 and form a track for the adapter 22 to rotate relative to the base 21. The inner wall 2153 protrudes from the outer surface of the housing 211*a* of the base 21 and surrounds the through hole 2151, and the inner wall 2153 is located between the groove 2152 and the through hole 2151. The at least one drainage hole 2154 is located at a bottom of the groove 2152. Accordingly, when water accidentally flows into the groove 2152 from a gap between the base 21 and the adapter 22, the inner wall 2153, which has a certain height in the structural design, can block the water from flowing into the through hole 2151, and the at least one drain hole 2154 can guide the water out of the groove 2152.

In one embodiment of the present disclosure, the base 21 further includes a pipe connector 216. The pipe connector 216 is disposed in a frame 2112 of the housing 211*c* and is located below the fixing portion 215. One end of the pipe connector 216 can be fluidly connected to the adapter 22, and the other end of the pipe connector 216 can be fluidly connected to the gas outlet 234 of the water tank 23. The pipe connector 216 can be made of silicone or similar materials such that an airtight effect can be provided when the pipe connector 216 is fluidly connected to the corresponding element. In this embodiment, the pipe connector 216 further includes a water guiding portion 2161. The water guiding portion 2161 is disposed on a periphery of the pipe connector 216 and a position of the water guiding portion 2161 is corresponded to a position of the at least one drainage hole 2154 of the fixing portion 215. Accordingly, when water flows out of the groove 2152 from the at least one drainage hole 2154, the water guiding portion 2161 can receive the water flowing through the at least one drainage hole 2154 to prevent the water from accidentally contacting the control element 212 and causing a short circuit.

The base 21 further includes a heating element 217. In this embodiment, the heating element 217 is disposed on the housing 211*b* of the base 21, and the heating element 217 is electrically connected to the control element 212. When the water tank 23 is combined with the base 21, the water stored in the water tank 23 can be heated by the heating element 217.

The adapter 22 includes a first end 221, a second end 222 and a flow channel 223. The flow channel 223 penetrates from the first end 221 to the second end 222 and serves as a fluid transmission path. The adapter 22 is combined with the fixing portion 215 of the base 21, and the first end 221 of the adapter 22 passes through the through hole 2151 and is in fluid connection with one end of the pipe connector 216. The second end 222 of the adapter 22 is configured to combine the heated circuit 30 to form a fluid connection. In one embodiment of the present disclosure, the adapter 22 can rotate at least 90 degrees relative to the base 21, but the rotation angle of the adapter 22 is not limited thereto. The adapter 22 further includes an electrical connection port 224. The electrical connection port 224 is disposed at the second end 222 and located at a periphery of the flow channel 223 such that the adapter 22 is electrically connected to the heated circuit 30 by the electrical connection port 224 when the adapter 22 is combined with the heated circuit 30. In addition, the electrical connection port 224 is electrically connected to the control element 212 via an electrical connection wire 225.

Figure 7:
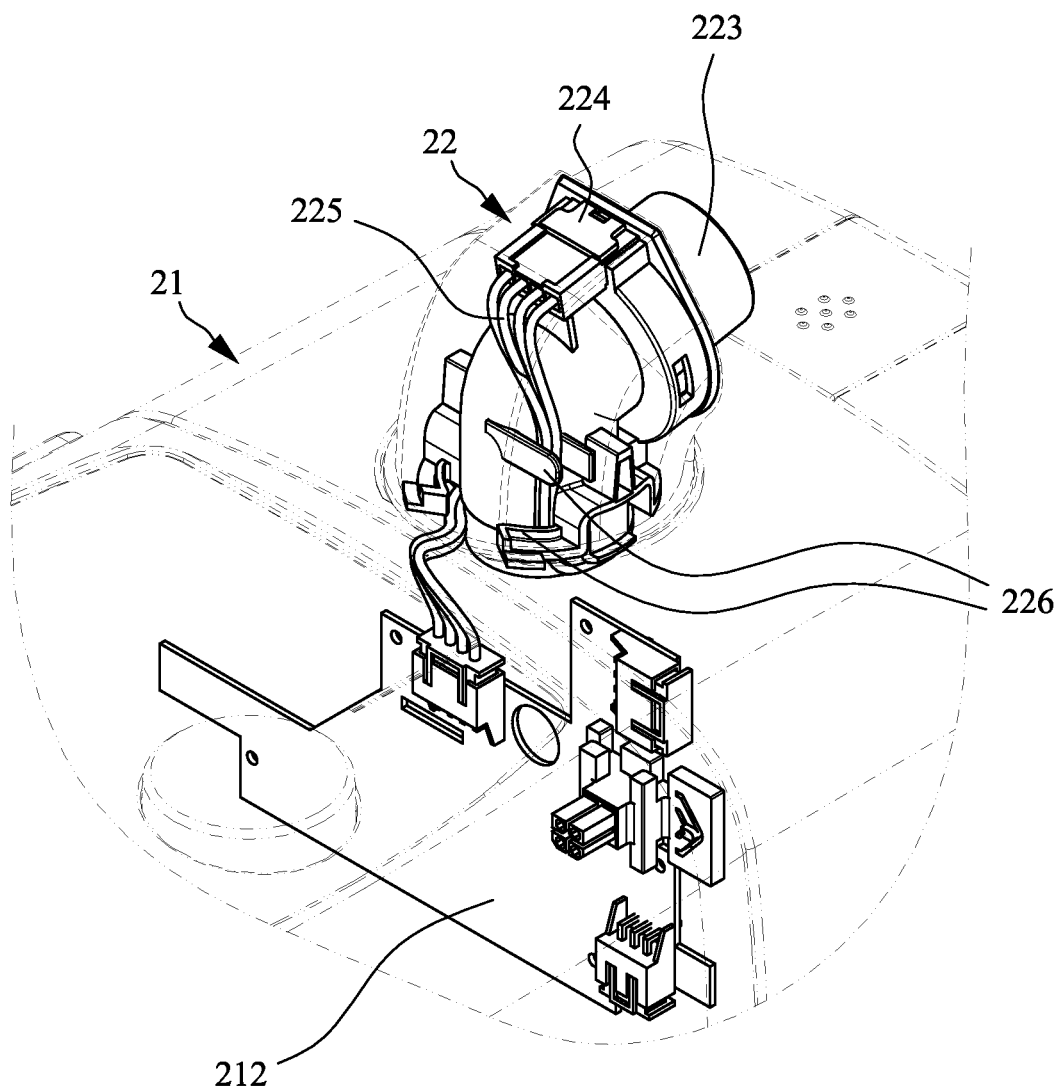
FIG. 7 illustrates a perspective view of the initial state of the adapter of the respiratory system of the present disclosure.
Figure 8:
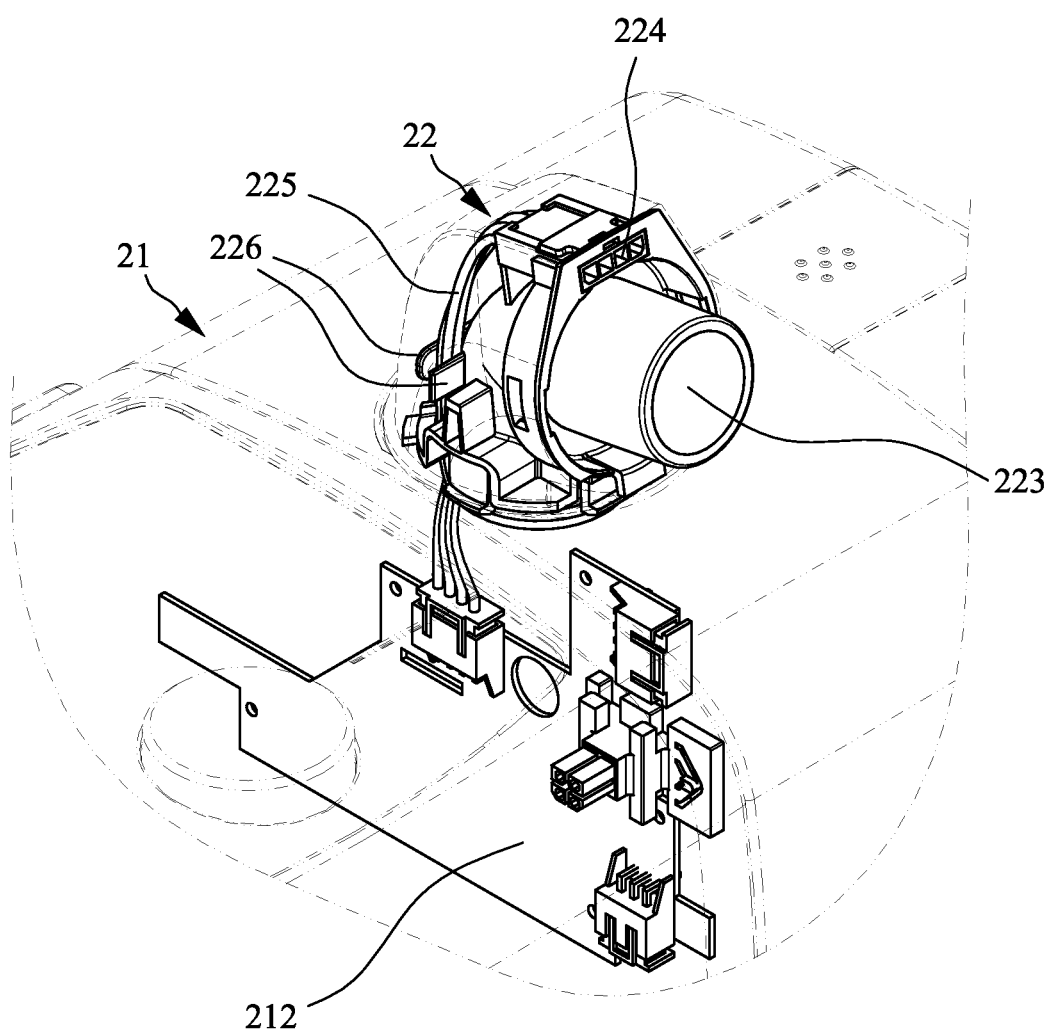
FIG. 8 illustrates a perspective view of the adapter of the respiratory system of the present disclosure rotated relative to the base.

Hereinafter, please refer to FIG. 6 to FIG. 8 together. FIG. 7 illustrates a perspective view of the initial state of the adapter 22 of the respiratory system 1 of the present disclosure, and FIG. 8 illustrates a perspective view of the adapter 22 of the respiratory system 1 of the present disclosure rotated relative to the base 21. As shown in FIG. 6 and FIG. 7, in one embodiment of the present disclosure, the adapter 22 further includes at least one wire restraint portion 226. The at least one wire restraint portion 226 is disposed on the periphery of the flow channel 223 of the adapter 22. Except the necessary length of the electrical connection wire 225 for connecting the control element 212 to the electrical connection port 224, additional length of the electrical connection wire 225 is additionally reserved for the rotation operation of the adapter 22. Accordingly, the electrical connection wire 225 arranged along the periphery of the flow channel 223 of the adapter 22 can be subjected to a wire restraint effect by the at least one wire restraint portion 226, and the additional length of the electrical connection wire 225 can be accommodated and wound around the at least one wire restraint portion 226.

As shown in FIG. 6 and FIG. 8, in this embodiment, the adapter 22 is rotated clockwise from the initial state of FIG. 7 by about 90 degrees relative to the base 21. At this time, the electrical connection wire 225 moves along the at least one wire restraint portion 226 as the adapter 22 is rotated. The arrangement of the wire restraint portion 226 of the adapter 22 prevents the electrical connection wire 225 from directly contact the base 21 when the adapter 22 rotates, so the electrical connection wire 225 will not rub the base 21 and thereby be damaged or broken. In addition, the design of the at least one wire restraint portion 226 of the adapter 22 can reduce a space requirement during the movement of the electrical connection wire 225, thereby improving the space configuration inside the structure. It should be noted that, in order to facilitate the visualization of the state of the electrical connecting wire 225 wound around the at least one wire restraint portion 226 and its connection configuration, the adapter 22, the base 21 and other structural components are shown in dotted lines in FIG. 7 and FIG. 8. It must be explained first here.

Figure 9:
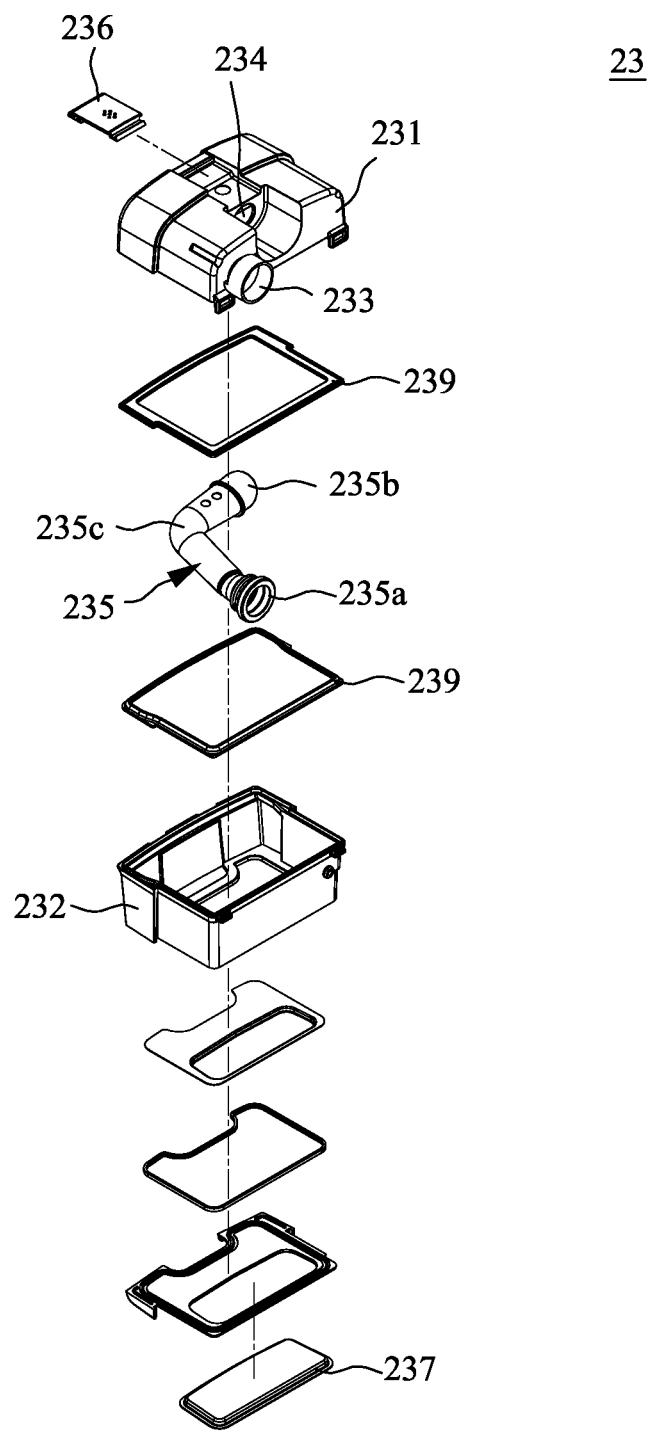
FIG. 9 illustrates an exploded view of the water tank of the heating and humidifying unit of the respiratory system of the present disclosure.

Please refer to FIG. 4 and FIG. 9 together. FIG. 9 illustrates an exploded view of the water tank 23 of the heating and humidifying unit 20 of the respiratory system 1 of the present disclosure. As shown in FIG. 4 and FIG. 9, the water tank 23 of the heating and humidifying unit 20 is detachably combined with the base 21. The water tank 23 includes a cover 231 and a reservoir 232 that can be combined. The water tank 23 can form an accommodating space after the cover 231 and the reservoir 232 are combined, and the cover 231 is located above the reservoir 232. The accommodating space inside the reservoir 232 can be filled with water for humidifying gas, and a scale of the filled water amount can be marked on an outer surface of the reservoir 232 as required. In one embodiment of the present disclosure, the cover 231 and the reservoir 232 can be locked and fixed to each other by corresponding snap structures, but the present disclosure is not limited thereto. In addition, at least one auxiliary sealing member 239 may be disposed between the cover 231 and the reservoir 232 to provide fluid sealing for a gap formed between the cover 231 with the reservoir 232.

The water tank 23 further includes a gas inlet 233, a gas outlet 234 and a sleeve member 235. The gas inlet 233, the gas outlet 234 and the sleeve member 235 are all disposed at the cover 231. When the water tank 23 is combined with the base 21, the gas inlet 233 can penetrate through the aperture 2111 of the base 21, and the gas outlet 234 can be in fluid connection with the pipe connector 216 of the base 21. The sleeve member 235 includes a buffer end 235a sleeved on the gas inlet 233, and the sleeve member 235 extends from the gas inlet 233 toward the water tank 23 to form a gas outlet end 235b. In order to adapt the limited space in the water tank 23 and extend a fluid flow path, in one embodiment of the present disclosure, the sleeve member 235 may form at least one curved part 235c, and the curved part 235c has an obtuse angle to maintain the smooth flow of fluid.

When the water tank 23 is combined with the base 21, the buffer end 235a of the sleeve member 235 is directly fluidly connected to the gas supply port of the gas supply unit 10 to provide flow channel sealing and combination buffering effects. Because the gas supplied by the gas supply unit 10 directly enters the water tank 23 without contacting the base 21, the possibility of gas leakage can be reduced. Here, the sleeve member 235 can also be made of silicone or similar materials such that a better airtight effect can be provided when the buffer end 235a of the sleeve member 235 is fluidly connected to the gas supply port of the gas supply unit 10.

In addition, in one embodiment of the present disclosure, the water tank 23 further includes a locking member 236. The locking member 236 is disposed in the cover 231, and the locking member 236 can be moved by force. When the water tank 23 is combined with the base 21, the locking member 236 and a corresponding locking member disposed on the base 21 are locked with each other to provide a stable combination of the water tank 23 and the base 21. When the locking member 236 is moved by force, a locked state of the locking member 236 and the corresponding locking member of the base 21 will be released so as to separate the water tank 23 and the base 21.

The water tank 23 further includes a heat conducting member 237. The heat conducting member 237 is arranged corresponding to the heating element 217 of the base 21, and a position of the heat conducting member 237 is adjacent to the reservoir 232. When the water tank 23 is combined with the base 21, the heating element 217 of the base 21 can directly contact the heat conducting member 237 of the water tank 23. Accordingly, when the control element 212 drives the heating element 217 to start heating, the heat conducting member 237 can receive heat energy from the heating element 217 by means of heat conduction and then heat the water stored in the reservoir 232.

Figure 10:
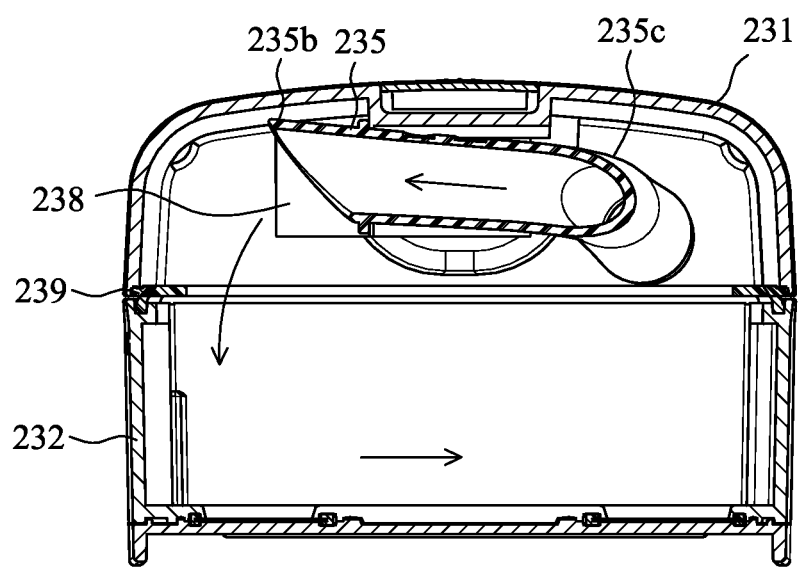
FIG. 10 illustrates a cross-sectional view of the water tank of the respiratory system of the present disclosure along the line B-B' in FIG. 4.
Figure 11:
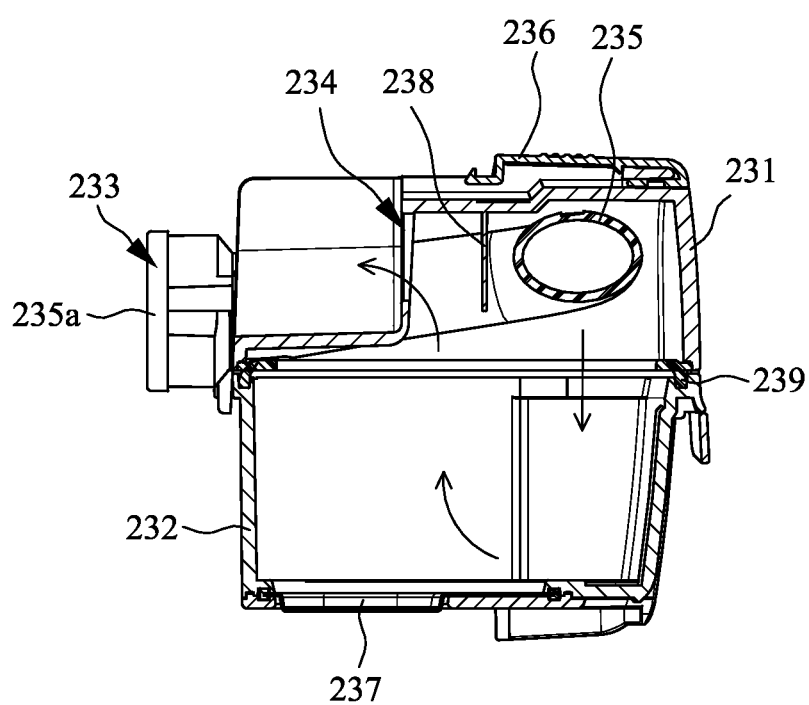
FIG. 11 illustrates a cross-sectional view of the water tank of the respiratory system of the present disclosure along the line C-C' in FIG. 4.

Please refer to FIG. 4, FIG. 10 and FIG. 11 together. FIG. 10 illustrates a cross-sectional view of the water tank 23 of the respiratory system 1 of the present disclosure along the line B-B' in FIG. 4, and FIG. 11 illustrates a cross-sectional view of the water tank 23 of the respiratory system 1 of the present disclosure along the line C-C' in FIG. 4. As shown in FIG. 4, FIG. 10 and FIG. 11, in one embodiment of the present disclosure, taking a bottom of the reservoir 232 as a comparison reference, the buffer end 235a and the gas outlet end 235b of the sleeve member 235 are both higher than the reservoir 232, and the gas outlet end 235b is higher than the buffer end 235a. Accordingly, the water stored in the reservoir 232 can be prevented from flowing back to the gas outlet end 235b to provide waterproof protection for the fluid path. In addition, a cross-sectional area of the sleeve member 235 gradually increases from the buffer end 235a to the gas outlet end 235b, and the gas outlet end 235b of the sleeve member 235 forms a chamfered surface facing the reservoir 232, thereby reducing the velocity of the fluid flowing along the sleeve member 235 and increasing the fluid flow.

In one embodiment of the present disclosure, the water tank 23 further includes at least one baffle 238. The at least one baffle 238 is disposed on the cover 231 to separate the gas outlet end 235b of the sleeve member 235 from the gas outlet 234 of the water tank 23, and the at least one baffle 238 guides the gas output from the gas outlet end 235b of the sleeve member 235 to flow toward the reservoir 232. Accordingly, the flow path and stay time of the gas in the reservoir 23 can be extended by the arrangement of the at least one baffle 238 such that the gas can be fully heated and humidified in the water tank 23.

The flow path of the gas in the water tank 23 of the heating and humidifying unit 20 will be described below. As shown in FIG. 4, FIG. 10 and FIG. 11, the gas supplied from the gas supply unit enters the water tank 23 of the heating and humidifying unit 20 through the gas inlet 233 of the water tank 23. The gas first passes through the buffer end 235a of the sleeve member 235 and moves along an inner pipe of the sleeve member 235 to the gas outlet end 235b. Because the gas is blocked by the at least one baffle 238, the gas leaving the gas outlet end 235b can move only straight forward or toward the reservoir 232 below. The gas moving straight forward will also start to move along the contour of the cover 231 and toward the reservoir 232 below after hitting the cover 231. After the gas enters the reservoir 232 and contacts the water in the reservoir 232, the gas is humidified by the water vapor in the water tank 23. Finally, the gas leaves the water tank 23 through the gas outlet 234 of the water tank 23.

As shown in FIG. 1 and FIG. 5, in one embodiment of the present disclosure, the heating and humidifying unit 20 further includes a shield member 24. The shield member 24 is pivotally and rotatably connected to the base 21. When the gas supply unit 10 and the heating and humidifying unit 20 are separated, the shield member 24 can be rotated to cover the side of the base 21 engaging the gas supply unit 10. At this time, the aperture 2111 of the base 21 and the gas inlet 233 of the water tank 23 can be shielded by the shield member 24 to prevent the entrance of foreign objects. The shield member 24 may include a plurality of accommodating parts 241. When the shield member 24 is rotated to cover the side of the base 21 combined with the gas supply unit 10, the corresponding electrical connection port 2121 and the corresponding engaging structure 213 are accommodated by the plurality of accommodating parts 241. Accordingly, damage to the corresponding electrical connection ports 2121 and the corresponding engaging structure 213 due to external force can be prevented, and structural interference with the shield member 24 can be avoided.

When the heating and humidifying unit 20 is to be combined with the gas supply unit 10, the shield member 24 can be rotated to the state shown in FIG. 1 such that the gas supply unit 10 can move towards the heating and humidifying unit 20 along a substantially horizontal direction without any structural interference by the shield member 24. When the gas supply unit 10 is combined with the heating and humidifying unit 20, the shield member 24 is located below the gas supply unit 10 and serves as a bottom reinforcement of the gas supply unit 10. The shield member 24 may further include at least one guiding structure 242. In the process of combining the gas supply unit 10 and the heating and humidifying unit 20, the gas supply unit 10 is guided to be aligned with the heating and humidification unit 20 and keeps moving in a straight line to facilitate the combination of the gas supply unit 10 and the heating and humidifying unit 20 by the at least one guiding structure 242 in cooperation with the corresponding guiding structure (not shown) at the bottom of the gas supply unit 10.

In summary, the respiratory system of the present disclosure adopts separable structure designs for different functional units. When any functional unit is damaged or malfunctioned, or users have different usage requirements, the users can change any single functional unit. This design can improve the ease of assembly of the respiratory system and reduce the usage cost. In addition, the heating and humidifying unit of the respiratory system of the present disclosure can provide a fluid transmission path to improve the heating and humidifying effect of the fluid, and the rotatable adapter and the heated circuit can increase the flexibility of use of the respiratory system.

The above detailed description is merely illustrative in nature and is not intended to limit the embodiments of the subject matter or the application and use of such embodiments. Moreover, while at least one exemplary example or embodiment has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, various changes can be made in the function and arrangement of elements without departing from the scope defined by the claims, which include known equivalents and foreseeable equivalents at the time of filing this patent application.

What is claimed is:

1. A respiratory system, including:
a gas supply unit including a gas supply port; and
a heating and humidifying unit being detachably combined with the gas supply unit, the heating and humidifying unit being electrically connected to the gas supply unit when combined with the gas supply unit, the heating and humidifying unit including:
a base including a control element;

an adapter combined with the base and able to rotate at least 90 degrees relative to the base, wherein the adapter is electrically connected to the control element; and a water tank being detachably combined with the base, the water tank including a gas inlet and a gas outlet, wherein when the water tank is combined with the base, the gas inlet penetrates through and protrudes from an aperture of the base to be fluidly connected to the gas supply port, so that a gas supplied by the gas supply unit directly enters the water tank without contacting the base to prevent leakage, wherein the gas outlet is fluidly connected to the adapter.

2. The respiratory system of claim 1, wherein the adapter is electrically connected to the control element through an electrical connection wire, the adapter includes at least one wire restraint portion, and the electrical connection wire can be accommodated and wound around the at least one wire restraint portion to prevent the electrical connection wire from contacting and rubbing the base when the adapter rotates.

3. The respiratory system of claim 2, wherein the at least one wire restraint portion is disposed on the periphery of a flow channel of the adapter.

4. The respiratory system of claim 1, wherein the base further includes a fixing portion for combining with the adapter, the fixing portion includes a through hole and an inner wall, and the inner wall protrudes from a surface of the base and surrounds the through hole.

5. The respiratory system of claim 4, wherein the fixing portion further includes a groove and at least one drain hole, the groove surrounds the through hole and the inner wall is located between the groove and the through hole, and the at least one drain hole is located at a bottom of the groove.

6. The respiratory system of claim 5, wherein the base further includes a pipe connector, the pipe connector is disposed under the fixing portion and forms a fluid connection between the water tank and the adapter, the pipe connector includes a water guiding portion, and a position of the water guiding portion is corresponded to a position of the at least one drain hole to receive the water flowing in from the at least one drain hole.

7. The respiratory system of claim 6, wherein the pipe connector is made of silicone materials.

8. The respiratory system of claim 1, wherein the water tank further includes a sleeve member, the sleeve member extends from the gas inlet toward an interior of the water tank to form a gas outlet end, and the sleeve member includes a buffer end sleeved on the gas inlet such that the buffer end is directly connected to the gas supply port when the water tank is combined with the base to provide flow channel sealing and combination buffering effects.

9. The respiratory system of claim 8, wherein the gas outlet end of the sleeve member is higher than a reservoir of the water tank, and the gas outlet end forms a chamfered surface facing the reservoir.

10. The respiratory system of claim 8, wherein a cross-sectional area of the sleeve member gradually increases from the buffer end to the gas outlet end.

11. The respiratory system of claim 8, wherein the gas outlet end of the sleeve member is higher than the buffer end to prevent a water stored in a reservoir of the water tank from flowing back to the gas outlet end.

12. The respiratory system of claim 8, wherein the water tank includes at least one baffle for guiding the gas output from the gas outlet end to flow toward a reservoir of the water tank.

13. The respiratory system of claim 1, wherein the heating and humidifying unit further includes a shield member, and the shield member is pivotally and rotatably connected to the base and provides a protective effect for the base when the gas supply unit is separated from the heating and humidifying unit.

14. The respiratory system of claim 13, wherein the shield member further includes a plurality of accommodating parts to accommodate at least one corresponding electrical connection port of the control element and at least one corresponding engaging structure of the base.

15. The respiratory system of claim 1, further including a heated circuit, wherein the heated circuit is detachably combined with the adapter, and an electrical connection and a fluid connection are formed between the heated circuit and the adapter when the heated circuit is combined with the adapter.

16. The respiratory system of claim 1, wherein the base further includes a heating element and the water tank includes a reservoir and a heat conducting member corresponding to the heating element, and the heat conducting member is adjacent to the reservoir.

17. A heating and humidifying unit, including:
a base including a control element;
an adapter combined with the base and able to rotate at least 90 degrees relative to the base, wherein the adapter is electrically connected to the control element; and
a water tank being detachably combined with the base, the water tank including a gas inlet and a gas outlet, wherein when the water tank is combined with the base, the gas inlet penetrates through and protrudes from an aperture of the base, so that a gas supplied by a gas supply unit directly enters the water tank without contacting the base to prevent leakage, wherein the gas outlet is fluidly connected to the adapter.

18. The respiratory system of claim 17, wherein the adapter is electrically connected to the control element through an electrical connection wire, the adapter includes at least one wire restraint portion, and the electrical connection wire can be accommodated and wound around the at least one wire restraint portion to prevent the electrical connection wire from contacting and rubbing the base when the adapter rotates.

19. The respiratory system of claim 18, wherein the at least one wire restraint portion is disposed on the periphery of a flow channel of the adapter.

20. The respiratory system of claim 17, wherein the base further includes a fixing portion for combining with the adapter, the fixing portion includes a through hole and an inner wall, and the inner wall protrudes from a surface of the base and surrounds the through hole.

* * * * *